United States Patent [19]

Allen et al.

[11] Patent Number: 5,222,499
[45] Date of Patent: Jun. 29, 1993

[54] METHOD AND APPARATUS FOR IMAGING THE ANATOMY

[76] Inventors: George S. Allen, 628 Westview Ave., Nashville, Tenn. 37205; Robert J. Maciunas, 6320 Chickering Woods La., Nashville, Tenn. 37215; John M. Fitzpatrick, 6301 Robin Hill Rd., Nashville, Tenn. 37205; Venkateswara R. Mandava, 910 Woodmont Blvd., Apt. 08, Nashville, Tenn. 37204; Hsuan Chang, 2120 Fairfax Ave., Apt. 12, Nashville, Tenn. 37212

[21] Appl. No.: 859,256

[22] Filed: Mar. 26, 1992

Related U.S. Application Data

[63] Continuation of Ser. No. 436,763, Nov. 15, 1989, abandoned.

[51] Int. Cl.⁵ .............................................. A61B 6/03
[52] U.S. Cl. ............................. 128/653.1; 606/130; 364/413.13
[58] Field of Search .................. 128/653.1, 653.2; 606/130; 382/6; 378/901; 364/413.13, 413.16, 413.18, 413.22

[56] References Cited

U.S. PATENT DOCUMENTS

| | | | |
|---|---|---|---|
| 4,086,492 | 4/1978 | Lodge et al. | 378/901 |
| 4,465,069 | 8/1984 | Basier et al. | 128/303 B |
| 4,608,635 | 8/1986 | Osterholm | 378/901 |
| 4,629,451 | 12/1986 | Winters et al. | 128/303 B |
| 4,674,046 | 6/1987 | Ozeki et al. | 364/313.18 |
| 4,710,716 | 12/1987 | Keren et al. | 128/653 A |
| 4,769,756 | 9/1988 | Webber et al. | 364/413.16 |
| 4,777,598 | 10/1988 | Kellar et al. | 364/413.22 |
| 4,791,934 | 12/1988 | Brunnett | 128/653 |
| 4,791,934 | 12/1988 | Brunnett | 128/653 R |
| 4,945,914 | 8/1990 | Allen | 128/653 R |

FOREIGN PATENT DOCUMENTS

| | | |
|---|---|---|
| 0160238 | 11/1985 | European Pat. Off. |
| 0955916 | 9/1982 | U.S.S.R. ............ 128/303 B |
| 2159943 | 12/1985 | United Kingdom. |
| 2212371 | 7/1989 | United Kingdom. |

OTHER PUBLICATIONS (List continued on next page.)

Primary Examiner—Ruth S. Smith
Attorney, Agent, or Firm—Kenyon & Kenyon

[57] ABSTRACT

The present invention pertains to a fiducial implant for the human body that is detectable by an imaging system. The invention is comprised of a first portion and a second portion. The first portion is configured to be detected by an imaging system when place beneath the skin. The second portion is configured for fixed attachment to a bone beneath the skin without penetrating entirely through the bone and without penetrating entirely through the bone and without fracturing the bone. The first portion is sufficiently large and comprised of a material for detection by an imaging system, and sufficiently small to avoid the distortion of the skin when placed at an interface between the skin and the bone. The first portion also has at least a portion which is spherical and defines a surface for cooperating with a tool for securing the second portion to the bone. Additionally, the placement of n fiducial implants, where $n \geq 4$ and an integer, into a portion of anatomy of the human body allows for the recreation of a particular image slice of the portion of the anatomy taken by an imaging system with respect to a first time period, at subsequent imaging sessions and also with different scan modalities. This provides a doctor with the ability to accurately follow the progress of the portion of the anatomy of interest. Moreover, the existence of an fiducial implants allows a target to be identified within the portion of anatomy relative to an external coordinate system. The portion of anatomy with the target may then be operated on, for instance, robotically, or precisely irradiated.

23 Claims, 8 Drawing Sheets

OTHER PUBLICATIONS

J. Cranio-Max.-Fac. Surg. 15 (1987), George Thieme Verlag, Stuttgart, DE, & NY, NY: Calvarial Growth after Linear Craniectomy in Scaphocephaly as Evaluated by X-ray Stereophotogrammetry.

British Journal of Orthodontics, vol. 13, 1986, pp. 151-157, B. Rune et al.: Roentgen Stereometry in the Study of Craniofacial Anomalies—the State of the Art in Sweden.

J. Neurosurg., vol. 60, Jan. 1984, pp. 166-173, Alberius et al.: Roentgen stereophotogrammetric analysis of restricted periods of neurocranial suture immobilazation in rabbits.

Acta Anat., vol. 117, 1983, pp. 170-180, S. Karger AG, Basel, Switzerland, Alberius et al.: Roentgen Stereophotogrammetric Analysis of Growth at Cranial Vault Sutures in the Rabbit.

The American Journal of Anatomy, 1983, Alan R. Liss, Inc., vol. 168, pp. 321-330, Alberius et al.: Kinematics of Cranial Vault Growth in Rabbits.

Acta Radiologica Diagnosis, vol. 24, 1983, Fasc. 4, pp. 343, 352, G. Selvik et al.: A Roentgen Stereophotogrammetric System.

American Journal of Orthod., Jun. 1980, vol. 77, No. 6, pp. 643-653, Rune et al.: Movement of maxillary segments after expansion and/or secondary bone grafting in cleft lip and palate: A roentgen stereophotogrammetric study with the aid of metallic implants.

Cleft Palate Journal, Apr. 1980, vol. 17, No. 2, pp. 155-174, Rune et al.: Movement of The Cleft Maxilla in Infants Relative to the Frontal Bone. A Roentgen Stereophotogrammetric Study with the Aid of Metallic Implants.

Dentomaxillofac. Radiol., vol. 8, pp. 5-13, 1979, Rune et al.: Motion of bone segments after surgicalorthodontic correction of craniofacial deformities.

Acta Radiologica Diagnosis, vol. 19, 1978, Fasc. 3, pp. 423-432, Claesson et al.: Roentgen Stereophotogrammetry for Evaluation of Liver Volume and Shape.

Annales Chirurgiae Et Gynaecologiae, vol. 67, pp. 82-84, 1978, Trope et al.: Antineoplastic-Drug Effect Evaluated with a New X-Ray Stereophotographic Measurement of the Tumour Volume.

The Anatomical Record, vol. 213, pp. 207-214, 1985 Alberius et al.: Volumetric Changes in the Developing Rabbit Calvarium.

The Journal of Bone and Joint Surgery, vol. 68B, No. 5, Nov. 1986, pp. 770-774, Mjoeberg et al.: Mechanical Loosening of Total Hip Prostheses.

Acta Radiologica Diagnosis, vol. 27, 1986, Fasc. 6, pp. 619-627, Herrlin et al.: Space Orientation of Total Hip Prosthesis-A Method for three-dimensional determination.

The Journal of Bone and Joint Surgery, vol. 66A, No. 8, Oct. 1984, pp. 1198-1210, Karrholm et al.: Changes in Tibiofibular Relationships due to Growth Disturbances after Ankle Fractures in Children.

Spine, vol. 14, No. 2, 1989, pp. 162-165, Bengt Sturesson et al.: Movements of the Sacroiliac Joints-a Roentgen Stereophotogrammetric Analysis.

American Journal of Orthod., vol. 81, No. 1, Rune et al., Jan. 1982, pp. 65-70, Rune et al.: Posteroanterior traction in maxillonasal dysplasia (Binder Syndrome).

Clinical Orthopedics and Related Research, No. 191, Dec. 1984, pp. 129-135, Walheim et al.: Mobility of the Pubic Symphysis.

Acta Orthop. Scan., vol. 54, pp. 408-416, Jun. 1983, Ryd et al.: Migration of the Tibial Component in Successful Unicompartmental Knee Arthtoplasty.

Hideyasu Watanabe: Neuronavigator [Nuro Nabigeita] Igaku no Ayumi, vol. 137, No. 6, 10 May 1986, pp. 451-452.

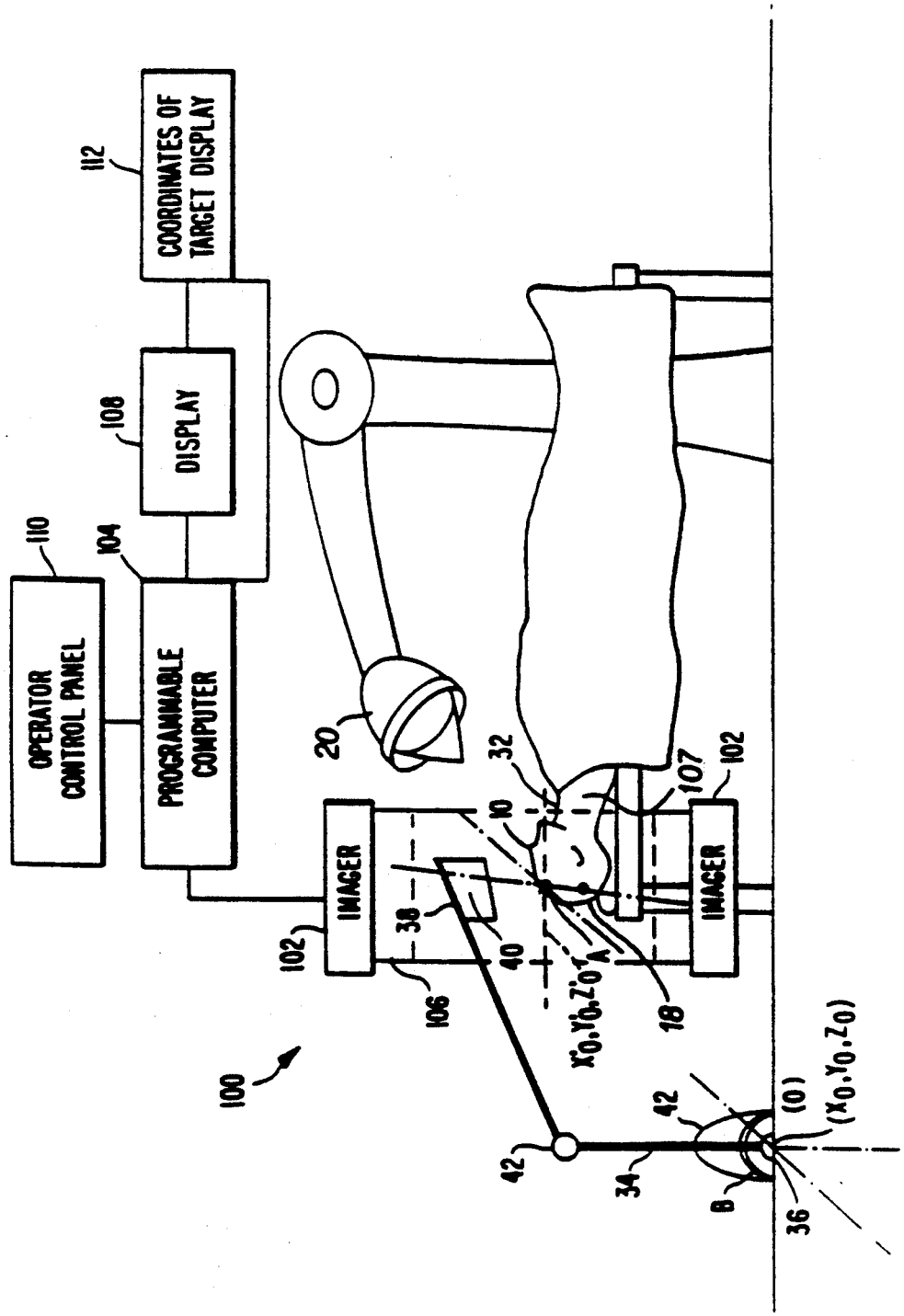

5,222,499

METHOD AND APPARATUS FOR IMAGING THE ANATOMY

This application is a continuation of application Ser. No. 07/436,763, filed Nov. 15, 1989 now abandoned.

BACKGROUND OF THE INVENTION

Diagnostic techniques that allow the practicing clinician to obtain high fidelity views of the anatomical structure of a human body have proved helpful to both the patient and the doctor. Imaging systems providing cross-sectional views such as computed tomographic (CT) x-ray imagers or nuclear magnetic resonance (NMR) machines have provided the ability to improve visualization of the anatomical structure of the human body without surgery or other invasive techniques. The patient can be subjected to scanning techniques of such imaging systems, and the patient's anatomical structure can be reproduced in a form for evaluation by a trained doctor.

The doctor sufficiently experienced in these techniques can evaluate the images of the patient's anatomy and determine if there are any abnormalities present. An abnormality in the form of a tumor appears on the image as a shape that has a discernible contrast with the surrounding area. The difference in contrast is due to the tumor having different imaging properties than the surrounding body tissue. Moreover, the contrasting shape that represents the tumor appears at a location on the image where such a shape would not normally appear with regard to a similar image of a healthy person.

Once a tumor has been identified, several methods of treatment are utilized to remove or destroy the tumor including chemotherapy, radiation therapy and surgery. When chemotherapy is chosen drugs are introduced into the patient's body to destroy the tumor. During the course of treatment, imagers are commonly used to follow the progress of treatment by subjecting the patient to periodic scans and comparing the images taken over the course of the treatment to ascertain any changes in the tumor configurations.

In radiation therapy, the images of the tumor generated by the imager are used by a radiologist to adjust the irradiating device and to direct radiation solely at the tumor while minimizing or eliminating adverse effects to surrounding healthy tissue. During the course of the radiation treatment, the imaging system is also used to follow the progress of the patient in the same manner described above with respect to chemotherapy.

When surgery is used to remove a tumor, the images of the tumor in the patient can guide the surgeon during the operation. By reviewing the images prior to surgery, the surgeon can decide the best strategy for reaching and excising the tumor. After surgery has been performed, further scanning is utilized to evaluate the success of the surgery and the subsequent progress of the patient.

A problem associated with the scanning techniques mentioned above is the inability to select and compare accurately the cross section of the same anatomical area in images that have been obtained by imagers at different times or by images obtained essentially at the same time using different image modalities, e.g., CT and MRI. The inaccuracy in image comparison can be better appreciated from an explanation of the scanning techniques and how the imaging systems generate the images within a cross-sectional "slice" of the patient's anatomy. A slice depicts elemental volumes within the cross-section of the patient's anatomy that is exposed or excited by a radiation beam or a magnetic field and the information is recorded on a film or other tangible medium. Since the images are created from slices defined by the relative position of the patient with respect to the imager, a change of the orientation of the patient results in different elemental volumes being introduced into the slice. Thus, for comparison purposes two sets of approximately the same anatomical mass taken at different times, do not provide comparable information that can be accurately used to determine the changes that occurred between two images selected from the respective sets share common views.

The adverse effects on the medical practice of such errors is exemplified by diagnostic techniques utilized by the surgeon or others in diagnosing a tumor within a patient. If a patient has a tumor, its size density and location can be determined with the help of images generated by a scanning device. For the clinician to make an assessment of the patient's treatment, two scanning examinations are required. The patient is subjected to an initial scan that generates a number of slices through the portion of the anatomy, for instance the brain, to be diagnosed. During scanning, the patient is held in a substantially fixed position with respect to the imager. Each slice of a particular scan is taken at a predetermined distance from the previous slice and parallel thereto. Using the images of the slices, the doctor can evaluate the tumor. If, however, the doctor wants to assess changes in the configuration of the tumor over a given period of time, a second or "follow-up" scan has to be taken.

The scanning procedure is repeated, but since the patient may be in a position different from that in the original scan, comparison of the scans is hampered. Slices obtained at the follow-up examination may be inadvertently taken at an angle when compared to the original slices. Accordingly the image created may depict a larger volume than that which was actually depicted before. Consequently, the surgeon may get a false impression of the size of the tumor when comparing scans taken at different periods. Because of this, slice-by-slice comparison cannot be performed satisfactorily.

Similarly for certain surgical techniques it is desirable to have accurate and reliable periodic scans of identical segments of the tumor within the cranial cavity. If the scans before and after surgery are inaccurate, the doctor may not get the correct picture of the result of surgery. These same inaccuracies apply to other treatments such as chemotherapy discussed above.

Additionally, with regard to imaging systems and the integral part they play in surgical and other tumor treatment procedures, there is a dearth of methods currently existing that allow a determination of a desired location within the body a given time. For example, U.S. Pat. No. 4,583,538 to Onik, et al. discloses a localization device that is placed on a patient's skin which can be identified in a slice of a CT scan. A reference point is chosen from a position on the device which exactly correlates to a point on the CT scan. Measurements of the localization device on the CT scan is then correlated to the device on the patient.

Exterior devices have been utilized in an attempt to solve some of these problems with accuracy such as that shown in U.S. Pat. No. 4,341,220 to Perry which discloses a frame that fits over the skull of a patient. The frame has three plates, each defining a plurality of slots on three of four sides. The slots are of varying lengths and are sequentially ordered with respect to length. Frame coordinates defined and found on the frame correspond to the varying heights of the slots. When slices of the skull and brain are taken by an imaging device, the plane formed by the slice intersects the three plates. The number of full slots in the slice are counted with respect to each plate to determine the coordinate of a target site with the brain. Accordingly, only one CT scan is needed to pinpoint the coordinates of the target.

Other attempts have included the use of catheters for insertion into the anatomy. For example, U.S. Pat. No. 4,572,198 to Codington discloses a catheter with a coil winding in its tip to excite or weaken the magnetic field. The weak magnetic field is detectable by an NMR device thus pinpointing the location of the catheter tip with respect to the NMR device.

SUMMARY OF THE INVENTION

Applicant's invention largely overcomes many of the deficiencies noted above with regard to imagers used heretofore. The invention relates to a method and apparatus for insuring that scans taken at different times produce images substantially identical to those of previous scans even if they are from different image modalities at different times. This insures that a more accurate assessment of any changes in anatomy is obtained. As a result, the doctor can be more certain as to the size, location and density of the tumor, or a section thereof, that is located in the cranial cavity.

This ability will enhance the use of surgical techniques in removing or otherwise eliminating the tumor in particular by those noninvasive techniques such as laser technology. By having the ability to define accurately the tumor location and size, laser beams can be focused directly on the tumor. Intermittently, as part of surgical techniques, scans can be made to determine if the tumor has moved or substantially changed in size as a result of the surgery. The laser or other surgical instrument can be adjusted accordingly. Because of the accuracy of the imaging techniques produced by the invention, the doctor can be confident that the amount of healthy tissue destroyed during surgery is minimized.

A method adopted by the invention disclosed herein utilizes fiducial implants or implants to define a plane which cooperates with the imager, or other computer, and particularly the data processing capabilities of the imager to insure that subsequent scanning results in slices substantially parallel to those taken during the initial scan. The fiducial implants are implanted beneath the skin into the calvania and are spaced sufficiently from one another to define a plane. The patient with these implants implanted is placed in the scanning device in the conventional manner and scanned to provide the images of consecutive parallel slices of a given thickness along a predetermined path through the cranial cavity.

As the scans are taken, one or more slices will be needed to accommodate part or all of each fiducial implant. The computational features of the imager or other computer will take into account the spatial relationship between any selected plane of a slice and that plane defined by the fiducial implants. Because of this capability, images taken in subsequent scans at different points in time, at different angles can be reconstructed to be substantially identical with the slices taken originally.

Fiducial implants for this purpose are specially configured and made of material that enables their implantation into the skull and the ability to be detected by scanning devices. The fiducial implant as disclosed herein is configured to insure that during implantation it does not have adverse effects on the skull such as cracking or extending through to the cranial cavity. Nor is it sufficiently exposed between the skull and the skin to distort any external features of the anatomy. Furthermore, the fiducial implant is positioned at least on a portion of the skull at the interface of the skin and the bone of the skull to facilitate its imaging by the imager. At least a portion of the implant is symmetrical in cross-section such that slices taken of the cranial cavity, for example, can be used to locate the center of mass of the implant. This insures accuracy in using the implant image as a reference point to transform the subsequent slices of the follow-up examination into the proper position and orientation.

The above has been a description of certain deficiencies in the prior art and advantages of the invention. Other advantages may be perceived from the detailed description of the preferred embodiment which follows.

BRIEF DESCRIPTION OF THE DRAWINGS

A more complete appreciation of the present invention and many of the attendant advantages thereof will be readily obtained, as the same becomes better understood by reference to the following detailed description, when considered in connection with the accompanying drawings, wherein:

FIGS. 1A, 1B, and 1C provide side and overhead views of fiducial implants, with the embodiment of FIGS. 1b and 1c including threading and hex-key structure not shown in the embodiment of FIG. 1a.

FIG. 7 is a side view of a preferred embodiment of the present invention.

DESCRIPTION OF THE PREFERRED EMBODIMENT

Figure 1A:
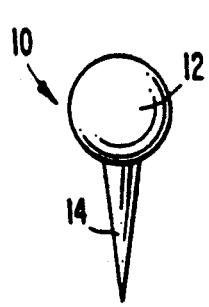
Figure 1B:
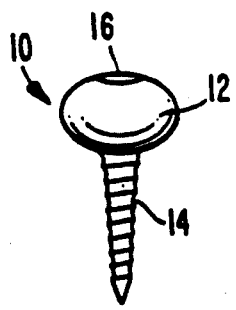
Figure 1C:
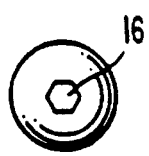

In FIGS. 1a, 1b, and 1c there is shown a fiducial implant 10 for the human body that is detectable by an imaging system. The fiducial implant comprises a first portion 12 and a second portion 14. The first portion 12 is configured to be detected by an imaging system (when place beneath the skin.) The second portion 14 is configured for fixed attachment to the bone beneath the skin without fracturing the bone. The first portion 12 is sufficiently large and comprised of a material for detection by an imaging system and sufficiently small to provide minimal distortion of the skin when placed at an interface between the skin and the bone. First portion 12 also has at least a portion which is spherical and defines a surface (such as indentational) for cooperating with a tool for securing the second portion 14 to the bone. Additionally, the placement of three fiducial implants 10 into a portion of anatomy of the human body allows of the recreation of a particular image slice of the portion of the anatomy taken by an imaging system in order to duplicate images taken at the first time period, that is, at the initial examination. This provides a doctor with the ability to accurately follow the progress of treatment on selected slices representing the anatomy of interest.

Moreover, the existence of three fiducial implants 10 allows a target (a tumor for instance) to be identified relative to an external coordinate system. The portion of anatomy with the target may then be operated on, for instance, robotically, or precisely irradiated.

To allow for the accurate comparison of image slices from at least two distinct periods of time, the three fiducial implants 10 are first implanted into a body of a patient at a desired region of interest. The patient is then placed in an imaging system and images of a series of cross-sectional slices are obtained that include, for example, the volume of the tumor which is the primary target of interest. From the imaging data obtained, the three fiducial implants are located and an internal coordinate system is defined with respect to them. If it is so desired, the image data may be further reformatted to show image slices whose direction is different from that obtained originally during the imaging period. Depending on the diagnostic information that these image slices reveal, appropriate decisions with regard to surgery, chemotherapy or radiation therapy on a patient may be made. The imaging data can also be used from several different types of images, such as CT, PET or NMR to obtain the same view of the anatomy but with different qualities stressed.

Figure 3:
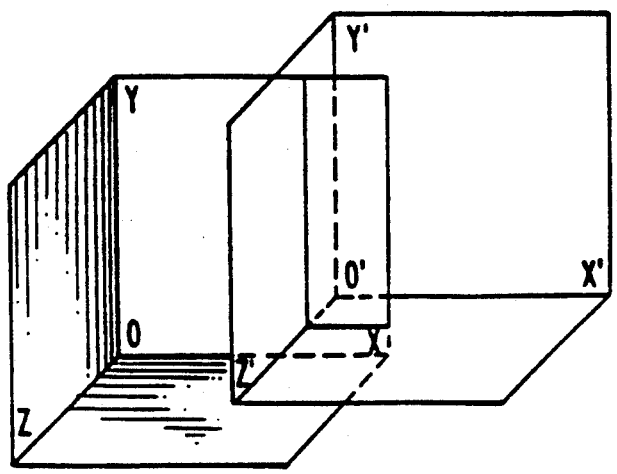
FIG. 3 is an offset view of two coordinate systems that have undergone translation with respect to each other.
Figure 4:
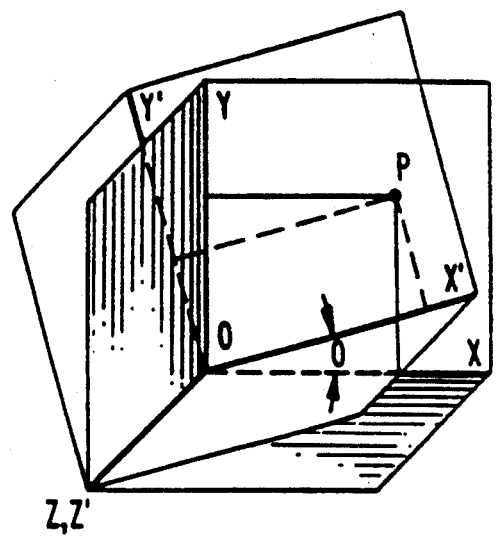
FIG. 4 is an offset view of two coordinate systems that have undergone rotation with respect to each other.
Figure 5:
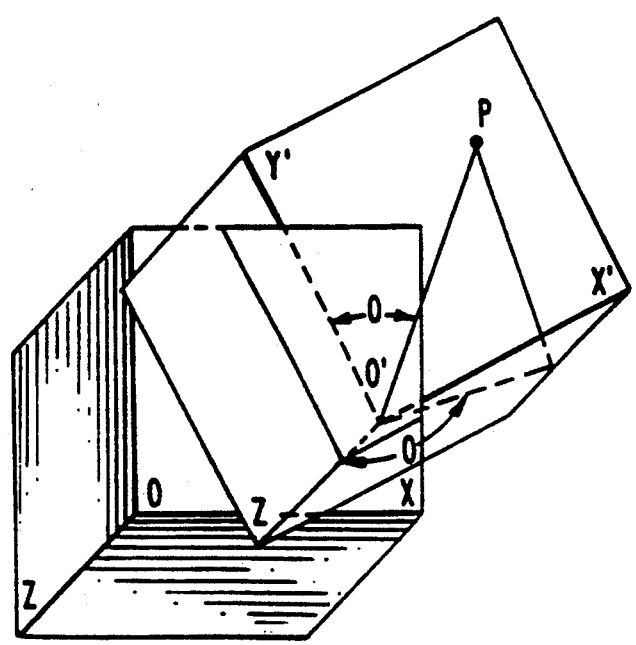
FIG. 5 and FIG. 5a, 5b and 5c are offset views of two coordinate systems that have undergone translation and rotation with respect to each other.

If it is decided to obtain further imaging data at a later time, then the patient is returned to the imaging system and the procedure for obtaining image data is repeated. The fiducial implants 10 are located with respect to the second imaging session and the same internal coordinate system is defined relative to the implants 10. Once the same internal coordinate system is defined with respect to the second imaging session, the translation and rotation of the internal coordinate system and the images with it is determined with respect to the coordinate system established at the first imaging session. See FIGS. 3, 4 and 5 for example. An image slice identified from the first imaging session that is to be used for diagnosis, is recovered from the second imaging session. The two image slices, one from the first image session and one from the second image session, are then compared to determine what changes, if any, have occurred in the anatomy of the patient.

More specifically, a 3-dimensional noncollinear coordinate system requires three distinct noncollinear points to be fully defined. If there are more than three identifiable points, the system is over-determined and three points have to be chosen to define the coordinate system. If there are less than three identifiable distinct points, the system is undetermined and a position relative to the one or two identifiable points will not be defined.

The known location of three distinct points identifies a plane upon which an orthogonal coordinate system can be established. If the three points are fixed in place relative to each other over time in the body, a coordinate system can be established that is also fixed in time. The ability to define a fixed internal coordinate system to the human body over time has important ramifications. A fully defined internal coordinate system that is fixed in place over time with respect to some location in the body permits comparison of subsequent images of the body taken into imaging systems such as CT scans, NMR scans or PET scans, to name a few. More precisely, these comparisons will allow a diagnostician to see what change, if any, has occurred within the body at a predetermined location.

By utilizing a fixed coordinate system relative to the body, the same coordinates can be compared over time. However, the tissue or body material is not necessarily fixed in place relative to a predetermined set of coordinates over time. After the passage of time, the tissue may have shifted, a change not uncommon following surgery. Nevertheless, the ability to compare various properties (depending on the type of images) of the tissue at the same coordinates and at different times is a great advantage for diagnostic purposes.

In principle, the three points (that are necessary) to define a coordinate system can be chosen in a variety of ways. In one embodiment with respect to the brain or head region, the two ears and a tooth, or the two ears and the nose may comprise the three points. Alternatively, an image slice of the skull could provide a set of points from which the three points would be chosen to create the coordinate system for the body. Preferably, three fiducial points that are implanted into the body, and create high contrast images during scanning, provide the most reliable way to define a coordinate system. Ideally the three points should be in the same approximate area of the body that is under analysis, and also should be identifiable and measurable by different imagery systems, such as CT imagers and NMR imagers. The use of such a system is described at length in copending application U.S. Ser. No. 119,353 (now U.S. Pat. No. 4,991,579) which is incorporated herein by reference.

Figure 2A:
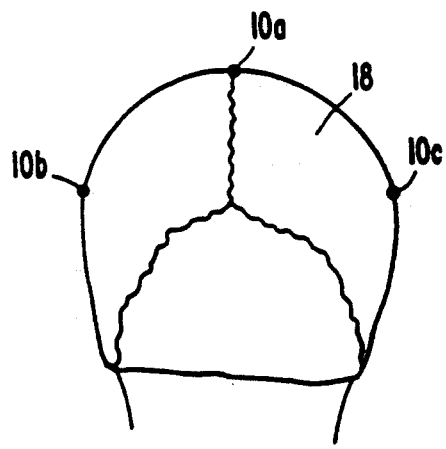
FIGS. 2a, 2b provide side and overhead views of a preferred positioning scheme of fiducial implants in the skull.
Figure 2B:
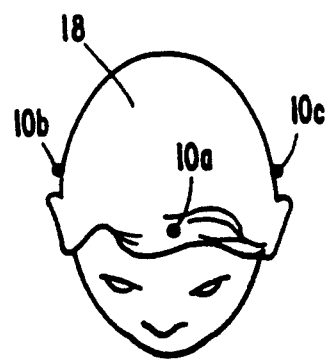

The placement of the three fiducial implants 10 depends on the portion of the anatomy to be evaluated. Essentially, three fiducial implants 10 are placed in three locations such that they are readily identifiable and the locations are fixed with respect to each other over time. If, for example, a study of the skull and brain is to be undertaken, preferably an implant 10A is placed on the midline of skull 18 just above the hairline, with the other two implants 10B, 10C being placed on the right and left side, respectively, of the midline in posterior position to the midline implant 10A. See FIGS. 2a and 2b which are a frontal and overhead view of skull 18, respectively. Another example of an area of interest could be the torso, with one fiducial implant 10 placed on the midline of the sternum and the other two fiducial implants 10 placed laterally thereto on the right and left side, respectively, and in ribs. Or, one fiducial implant 10 can be placed in the spinous process of a vertebra in the midline and the other two fiducial implants placed in right and left iliac crest, respectively.

Imaging apparatus provides a fixed axis relative to which any other position in space can be located. As a result, the position of the fiducial marker and the coordinate system these markers define can be located relative to the imaging apparatus. The features of the invention permit the location of the markers relative to the imaging apparatus to be recorded for future reference. In subsequent scans, the patient's orientation may change relative to the imaging apparatus. This new orientation can be measured by locating the fiducial markers in relation to the image apparatus and comparing it to the previously recorded location. The comparison technique permits re-orienting images of subsequent scans to a position corresponding to the earlier recorded scale so that image slices are always at generally the same cross-section of the earlier recorded slices.

In actual operation, these positions are defined by a coordinate system and it is the positioning of these systems that is accomplished by translation or rotation as discussed below.

Figure 5A:
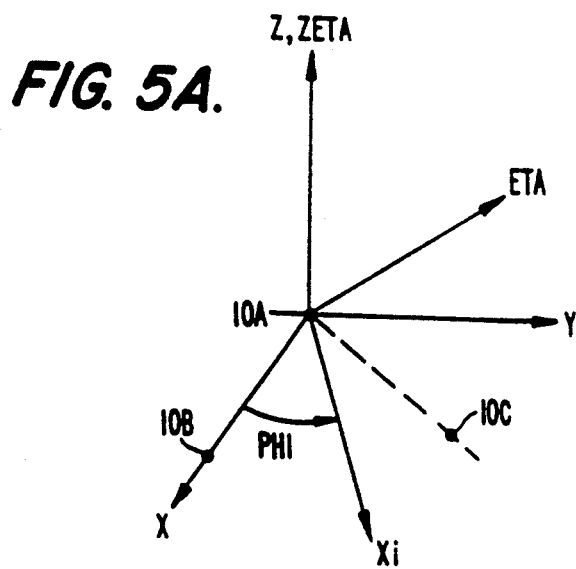
Figure 5B:
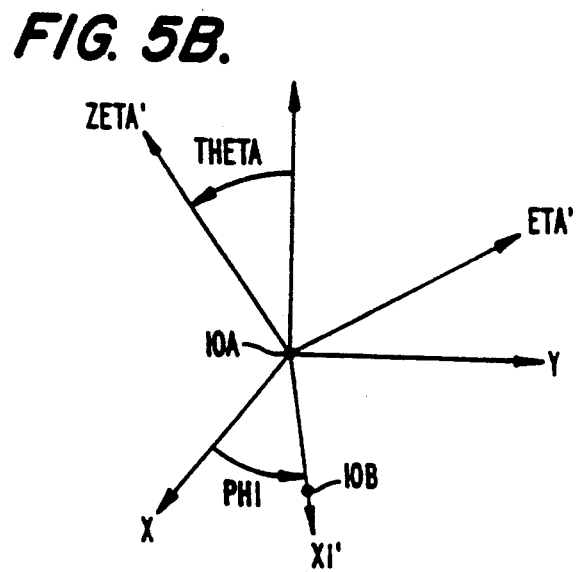
Figure 5C:
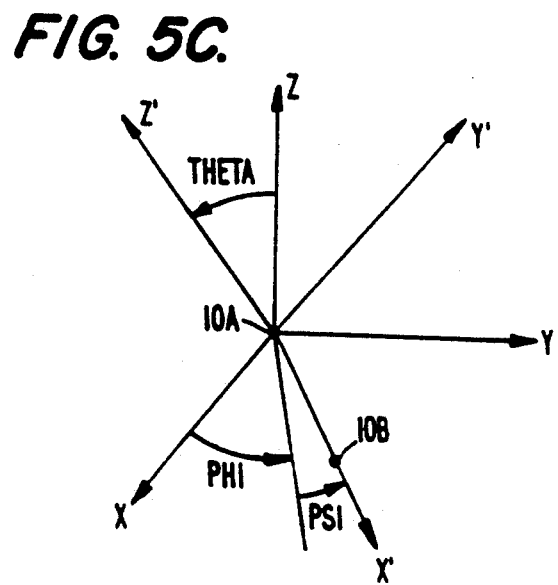
Figure 6:
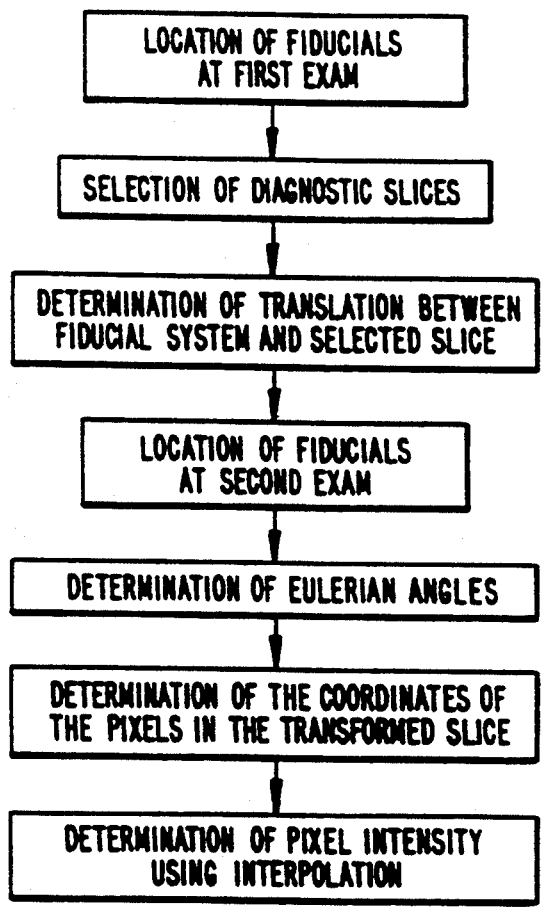
FIG. 6 is a flow chart with respect to determining the same point P at two different times in an internal coordinate system to the body.

Once the fiducial implants 10 are in a place and a coordinate system defined, subsequent images of the same anatomical volume area can be compared. If, for example, images of the brain are being taken, a person's head may be placed below, above, or to the side (see FIG. 3) of its location at a previous imaging session. The head might have undergone rotation and translation as compared to a previous imaging session (see FIG. 5). Regardless of the reasons why the head is oriented differently, by taking advantage of the fixed fully-defined internal coordinate system in the brain, a previous point or slice image of the brain can be obtained from subsequent information. This is accomplished as shown in FIG. 6, by comparing the location and direction of the plane defined by the three fiducial points at the first examination with the location and direction of the same plane defined by the three fiducial points at the time of the second examination. For simplicity, the origin of the coordinate system is located at a given fiducial point. By measuring the distance in say, the x, y and z directions between the same fiducial points (the origins) at the two different times, the translation of the origin of one coordinate system with respect to the other can be obtained. See FIGS. 5A, 5B and 5C.

Any point can be obtained with respect to translation and rotation of a given cartesian coordinate system. Since any point can be obtained, any plane can also be obtained, because a plane is comprised of a set of points. For example, if a given point is desired to be looked at over time, then the coordinate of the point is identified with respect to a first time. The translation and rotation information corresponding to the coordinate system at the first time with respect to the second time is then applied to the point at the first time to indicate the coordinates of the identical point in the coordinate system at the second time. The imaging data pertaining to the second time is then searched to find the desired point. This is but one way of many possible ways to obtain the same point in the coordinate system as a function of time.

Similarly, for a plane or slice image, the same procedure is applied to each point of the set of points that make up the slice image. The desired points are then searched for in the image information corresponding to the coordinate system at the second time. Once all the points, with their associated image information are identified, they are reformatted to produce an image slice as close as possible to the desired image slice pertaining to the coordinate system at the first time. Of course, the position of the slice selected by the physician from the initial image slices has to be determined with respect to the fiducial implants. To this end, preferably, the z coordinates or the elevation coordinates of the system have to be introduced. This can be done with respect to any slice in the image set. For instance, the slice containing the first fiducial implant can be chosen.

Ideally, the reformatting step takes image points from image slices of the second time and aligns them together and produces an image slice as similar as possible to the desired image slice of the first time. In practice, however, quite often a point that is necessary for the creation of a reformatted image does not exist because image slices were taken, for instance, above and below the point. In this case, interpolation must be used to estimate the attributes of the missing point so a desired image slice can be prepared. For example, one simple method of interpolation utilizes the two closest known points to the nonexistent desired point. These two known points are also as nearly opposite each other as possible with the desired point therebetween, and their average thus approximates the desired point's image value. For example, if the intensity of the image associated with one point is 6 units on a scale of 1 to 10 units and that of the second point is 4 units, and the two points are essentially equal in distance from the desired point, the desired point is assigned an image intensity value of 5 units. See FIG. 6, which shows the flow chart describing the above overall process.

Interpolation could be avoided if the internal coordinate system is positioned identically at the different times the imaging data is obtained. This could be accomplished by causing the three fiducial implants 10 to be exactly the same position whenever imaging data is obtained. By having, for instance, an X-ray machine, or following the method discussed below that reveals the location of the fiducial implants in the body with respect to an external coordinate system, and knowing where the implants were positioned at the first time that imaging occurred, the body could be moved to be in the same exact location. One way of moving the body in position is with a table or platform that has 3 dimensional movement. Then, knowing where the coordinate system is in the body with respect to the platform, the platform could be moved up, down, forward, backward and/or rotated so the internal coordinate system is positioned exactly the same way it was the first time imaging data was obtained.

To summarize, and referring to FIG. 6, the procedure consists of the following steps:

1. Locating the fiducial implants in the initial examination image set, and establishing the internal coordinate system;
2. Selection of the slice(s) of interest in the initial set;
3. Determination of the translation distance between the coordinate system determined by the fiducial implants and the selected slice;
4. Localization of the fiducial implants in the follow-up study;
5. Determination of Eulerian angles in the coordinate system;
6. Determination of the coordinates of each point in the transformed slice corresponding to the selected slice in the initial system;

7. Determination of the intensity values at each point using interpolation in the axial direction. (Axial direction is defined as the direction of motion of the imager table).

Although there are many different hardware and software embodiments to implement processing of the image data, each can be divided according to its functioning as follows:

(1) hardware that facilitates fast reconstruction of the cross sectional image;
(2) operator-interactive image display;
(3) storage device for images;
(4) hardcopy capability for images.

One embodiment utilizes the existing computer and its peripherals to generate the reformatted images.

Another embodiment utilizes a stand-alone system, in which the images are fed from the respective imager, and then perform the comparative analysis in the stand-alone system. The whole computer part of the imager must be essentially duplicate plus various options for data input supplied, in order to accommodate images of all types. Hardcopy capability is also desirable therein, such as a matrix camera, because permanent records are invaluable to the diagnostician.

Whether a stand-alone system or an existing system is modified for implementation of the above described reformatting, the images are preferably stored as files having two parts: (1) the header that contains the patient's demographic data and information on the examination itself, that is, technical parameters of the exposure or image procedure; and (2) the image matrix. These two parts are preferably stored temporarily (for a couple of days, usually) on magnetic disk drives, and then moved to permanent storage medium, such as magnetic tape or floppy disk. In addition to this file structure, a subfile may be added containing the results of the computation (the Euler angles may be added, for instance).

An apparatus 100 carries out the imaging, signal processing and display necessary to provide images of essentially the same coordinates in the human body which can be compared over time, or to provide the location of targets, such as tumors is shown in FIG. 7. Such an apparatus 100 is comprised of an imager 102 that supplies imaging data and is controlled by a programmable computer 104. The imaging data is obtained from a source 106 in the imager 102 that is approximately placed about a patient 107 as is well known in the art. The imaging data experiences signal processing, as described above, and the desired images are displayed on display 108. Additionally, operator interaction can be achieved through an operator control panel 110 and the coordinates of a target can be displayed in the coordinates of the target display 112 for radiation therapy applications.

The apparatus 100 operates in the following manner. A number of fiducial implants 10 are implanted in the region of interest in a patient 107, in the skull 18 for example. Once the fiducial implants 10 have been secured, the patient 107 is then placed within scanning range of the imager 102. A series of image slices is then created by performing a scan in a conventional manner. These image slices (the "image scan") are then stored in a data base library of the programmable computer 104.

The apparatus 100 allows the image scans (or slices of these scans) to be transformed into new images for display or comparison against a more recently obtained image scan of the patient 107. The following describes the operation of the programmable computer 104, once image scans have been acquired into some type of data storage device, such as magnetic tape.

The programmable computer's operation is window-based. It reads archival tapes and writes into the data base library, reads images for viewing from the data base, and calculates and performs transformations and other related functions. The operation has been implemented in the 'C' programming language and can be run, for example, on a SUN workstation, manufactured by SUN Microsystems, Inc., using the SunOS Release 4.0 operating system.

The data base library is in a hierarchical format that provides easy access and preserves the integrity of the data. The data base library contains one patient directory for each patient. Under each patient directory, there exists one scan directory for each image scan that has been taken of the patient. The scan directory contains several data files, which in turn contain all the data necessary to recreate an image scan, or a slice of an image scan, on the terminal screen.

Access to the data library is accomplished via a read/write capability of the computer 104. The user causes the computer 104 to read patient data out of storage (such as magnetic tape) and write it into the data base library. The user can also display the images contained in the data base library, and modify or transform those images into new images which may then be displayed on the display 108.

The data accessing operation described above is illustrated as a flow chart in FIG. 9. A data storage device, such as standard magnetic tape, is loaded with raw data during the scanning process in step 301. The computer 104 is programmable to read virtually any given data format from the data storage device or from the imager 102 itself. Referring to input step 303, the user then indicates which data format is being used and which image scan or slices of image scans from the data storage device are to be transferred to the data base library. The computer 104 then converts the data format from the data storage device into a format usable by the computer 14 in step 305. This conversion of formats does not alter the data but merely rearranges it into the proper form for the computer 104. The re-formatted data is then written into the data base library, step 308, where is it stored for future use.

Figure 10A:
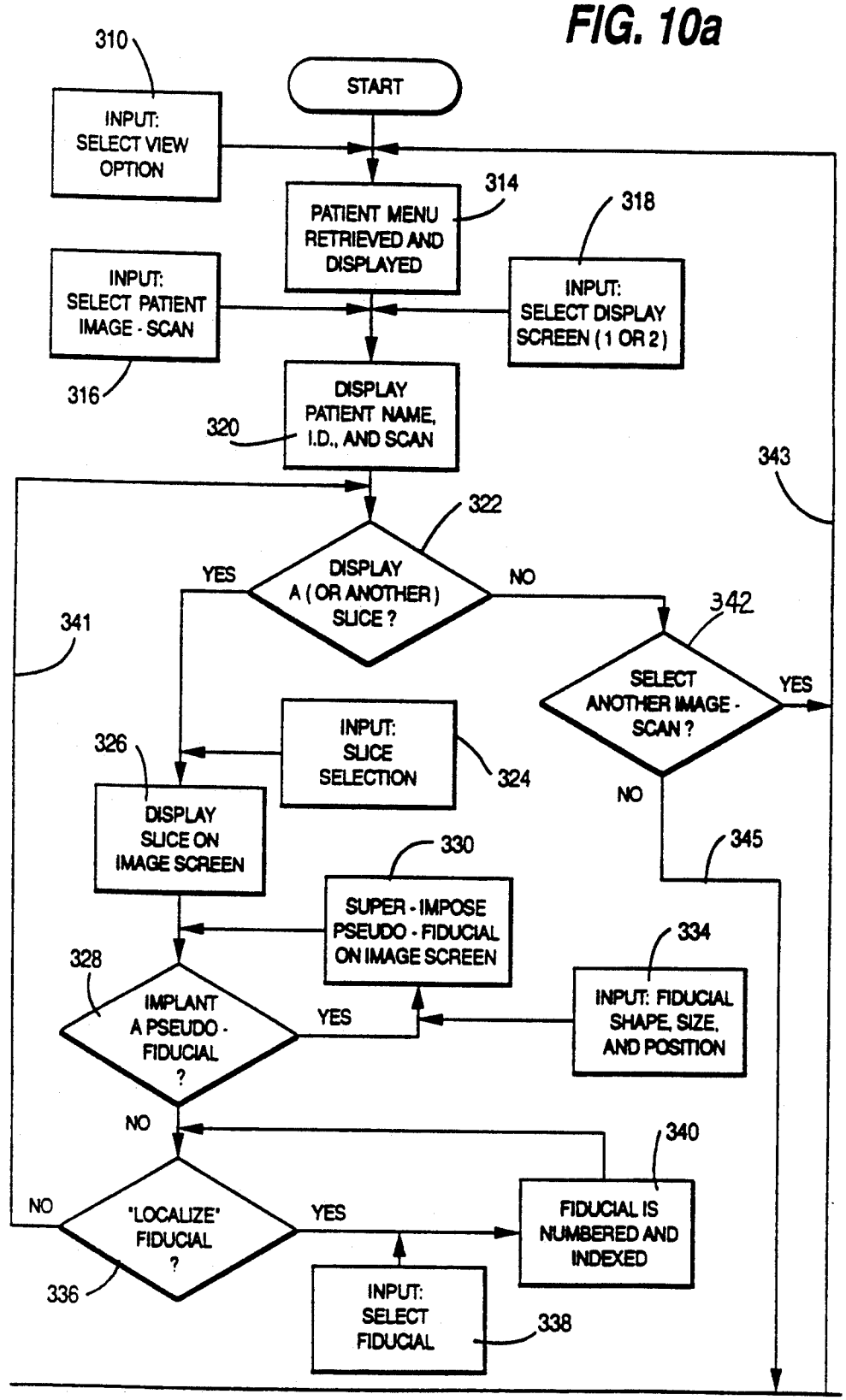
FIG. 10a and 10b illustrates a viewing and transformation process according to an embodiment of the present invention.
Figure 10B:
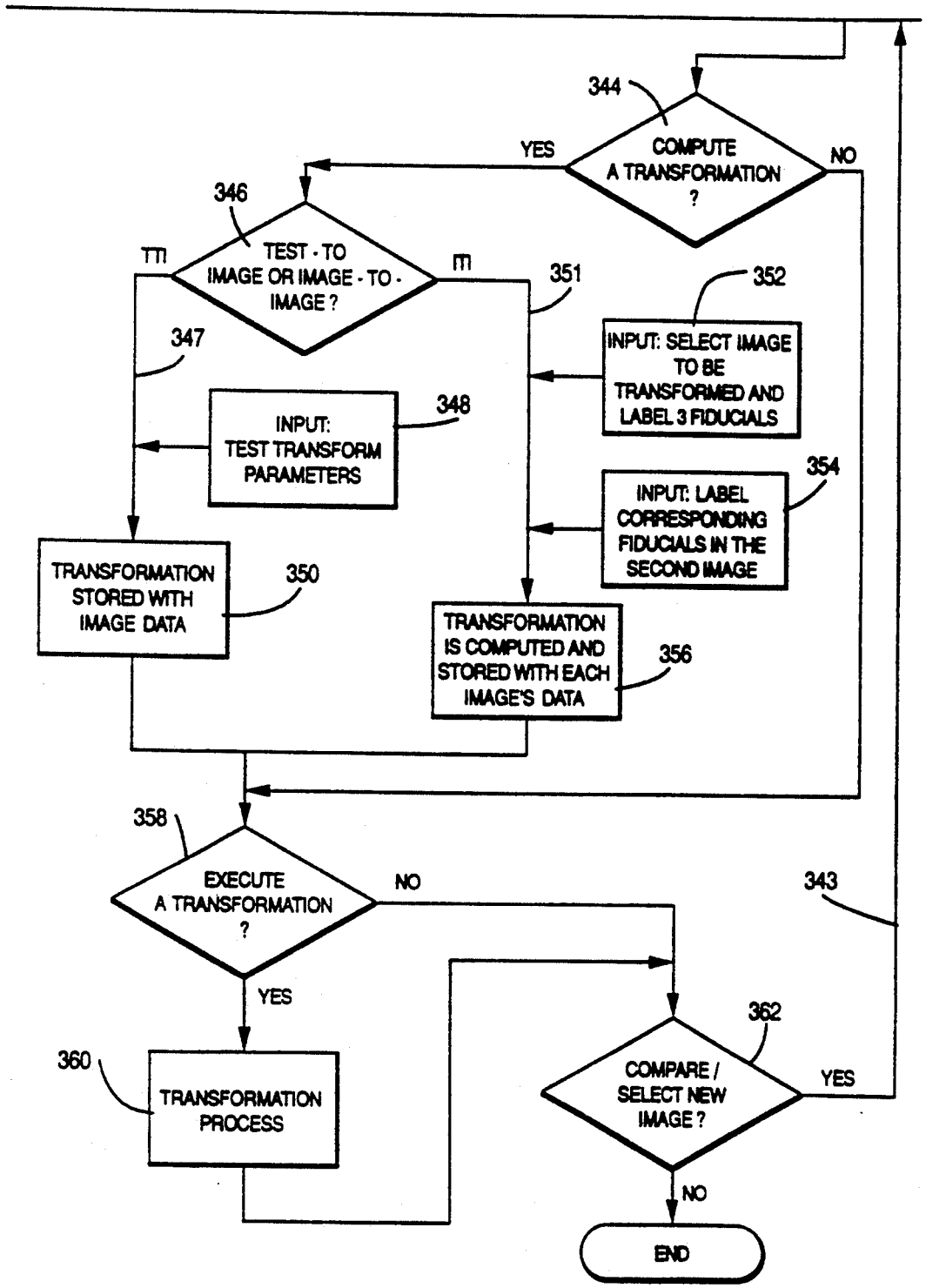

The operation of computer 104 to view and transform slices is illustrated by the flow chart in FIGS. 10a and 10b. The user first selects a view option in input step 310 whereupon the data base library is accessed to retrieve a patient menu which is displayed on the screen in display step 314. The user then selects a patient and an image scan of that patient in input step 316, and assigns the image scan (input step 318) to either of two display screens of display 108. The patient's name, I.D., and the name of the scan are displayed beneath the selected display screen in display step 320. The user now has the option to display a slice of the image scan in decision step 322. Assuming the user chooses to do so, the user then inputs which slice is to be viewed in input step 324. This is done by either selecting the proper slice number, or by selecting a group of slices which are displayed in miniature and picking the individual slice from the group. Slices are then displayed on the appropriate image screen in display step 326.

The user then has the option in decision step 328 of implanting pseudo-fiducials into the displayed slice. Pseudo-fiducials are computer generated reference points that are additional to the actual fiducial markers. These additional reference points can be used later to compute and execute transformations. If the user elects to exercise this option, the pseudo-fiducial shape, size, and the position are inputted in input step 334. After the proper inputs have been made, the computer 104 will superimpose the pseudo-fiducial onto the slice on the display screen 108 in display step 330. The user may repeat the implanting process, and implant up to nine pseudo-fiducials in any given slice.

The user may then choose to "localize" any fiducials in the slice, including both the pseudo-fiducials and the actual fiducials, in decision step 336. The purpose of the localization process is to identify the exact center of a fiducial so that the computer may use these coordinates when it calculates and performs a transformation. The center of the fiducial is determined manually by the user in input step 338. The user indicates this fiducial center by moving the cursor to the center of the fiducial and pressing the appropriate button. Since fiducials are three-dimensional objects which may occupy space in more than one slice, it is important that the user not only select the center of the fiducial on any particular slice but also that the user selects the particular slice which cuts through the center of this particular fiducial. After the user has made the center selection, the computer 104 then numbers the fiducial and records its coordinates for future reference in step 340. The user may localize as many other fiducials in the slice as desired.

After the user has implanted fiducials and/or localized the fiducials in a slice, or has elected not to do so, the user may then display any other slices in this image scan and repeat the same process (following path 341 back to decision step 322). After viewing the slices of the selected image scan, the user may then proceed to decision step 342, where the user has the option of selecting another image scan for simultaneous viewing. If simultaneous viewing is selected, operation of the computer 104 follows path 343 back to display step 314 and another image scan is selected. The second image scan can be assigned to the second display screen of the display 108 to thereby allow the user to view both the first and the second image scans at the same time, and compare the two image scans.

After the user has selected one or two image scans and localized fiducials within them, path 345 is followed to decision step 344, where the user is presented the option of computing a transformation. Decision step 346 allows the user to choose: 1) to calculate the transformation of one displayed image scan onto the second displayed image scan; or 2) to calculate the transformation of one displayed image scan according to test parameters which the user will input. If the user to chooses to input his own parameters (path 347), the three Eulerian angles which are associated with the transformation are input in input step 348. These parameters are then stored with the image scan data (step 350) in the data base library where they will remain until the transformation is executed.

Alternatively, if the user has chosen to calculate the transformation of one displayed image scan onto the other displayed image scan, path 351 is followed. In input step 352, the user selects which image scan is to be transformed, and labels three of the fiducials in that image as primary fiducials. These three primary fiducials must have been previously localized. The computer 104 uses the coordinates of these fiducials to determine the coordinate system for the entire volume of the image scan. The user then proceeds to the second image scan (to which the first image scan is being transformed) and labels the corresponding three fiducials in the second image scan. It is the user's responsibility to insure that the proper fiducials in each of the scans has been labeled so that the computer 104 may properly calculate the transformation.

The user then inputs a rough guess as to what the transformation will be in terms of its Eulerian angles. Using this guess as a starting point, the computer 104 calculates the exact transformation in step 356. This calculation is performed by method of trial and error in an algorithm that repeatedly refines the Eulerian angles until the transformation results in a coordinate match-up between the three primary fiducials and the image being transformed and the three primary fiducials in the image which is being transformed to. The computer transformation is then stored with each image scan's data in the data base library.

After a transformation has been calculated and stored, the user then has the option of executing it in decision step 358. The execution of a transformation in step 360 involves the mathematical process outlined above. Briefly, all the slices in an image scan are assembled and normalized into one volume. Individually the slices are not of uniform thickness, and thus have ragged edges. Therefore, the slices may not fit together exactly, which leaves holes between them where the ragged edges will not properly join. The computer 104 fills these holes in the image scan volume by interpolating between the closest available points, and thus approximates the proper data for the holes.

When all the holes are filled and the image scan volume is complete, the transformation may then proceed. The entire image scan volume is indexed from the three primary fiducials, and a new slice angle is selected pursuant to the Eulerian angles which have been previously calculated or input. The image scan volume is then uniformly sliced at this angle, and the new slice data of the transformation replaces the old data of the original image scan. In the interest of preserving memory space, the computer 104 preferably, eliminates the old data which may be re-read out of the data storage device if it is needed. The transformed image scan is assigned to the same screen where the original image scan was assigned The user may now compare slices of the transformed image scan with slices of the image scan to which it was transformed in decision step 362 and path 343. The entire viewing and transformation process may be repeated as desired.

Figure 9:
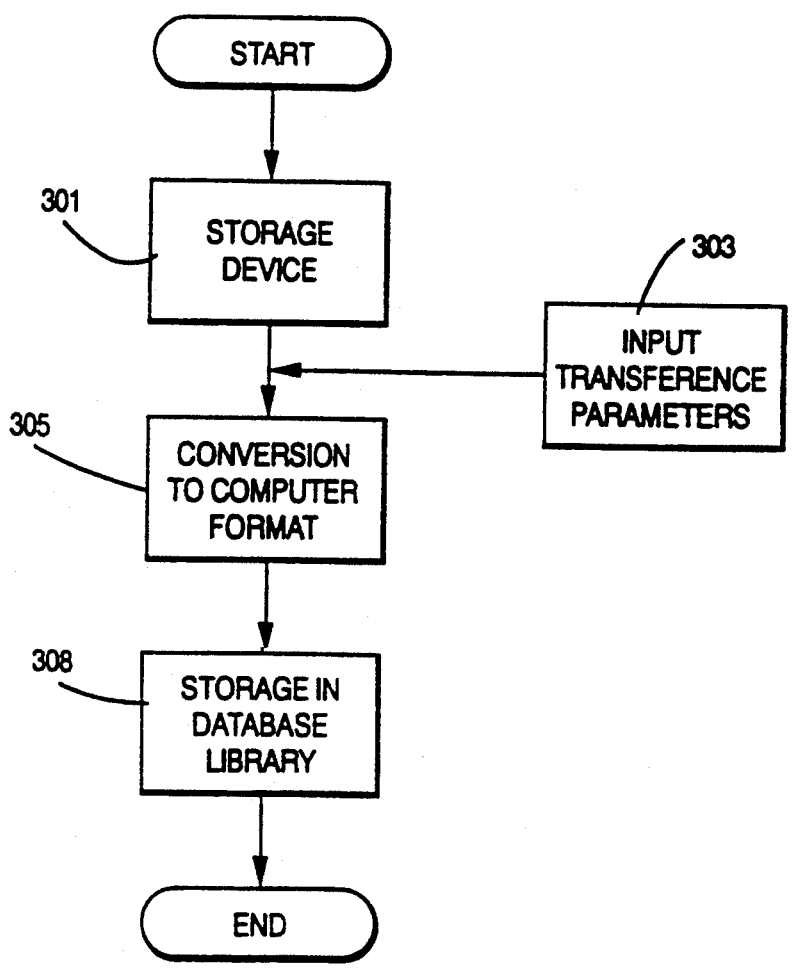
FIG. 9 illustrates a flow chart of a data accessing operation according to an embodiment of the present invention.

In addition to the functions outlined by the flow chart in FIGS. 9 and 10, the computer 104 has several additional features. A distance measurement function provides the user with a measurement of any distance within the image scan volume. The user merely selects a point A on any given slice and a point B on that or any other slice in the image scan volume. The computer 104 will calculate the distance between the two points and display the result. The computer 104 also contains a trace function which allows the user to trace a line around any feature of a displayed slice. The user may also use the trace function to trace simultaneously on a pair of slices displayed on the two image screens. The trace and distance functions allow accurate measurement and comparison of the relative sizes of tumors or other features found within the patient 107. This leads to more effective evaluation of improvement or decline in the patient's condition.

An application that takes advantage of a fully-defined internal coordinate system of the body relates to radiation therapy. For radiation therapy the location of a radioactive beam of an external coordinate system must be related to the internal coordinate system. See FIG. 5, where the external coordinate system can be considered the unprimed system and the internal system the primed system. The point P can represent the location of a point of a tumor. In this situation the actual distances and locations of the point P in the primed coordinate system, and the location of the origin S of the primed coordinate system are important If the point P is known with respect to the internal or primed coordinate system, and the primed coordinate system is known with respect to the external or unprimed coordinate system, and the Euler angles of rotation are known, then the location of point P is known with respect to the external coordinate system. For example and referring to FIG. 7, in radiation therapy or surgery knowing where the internal coordinate system A is with respect to an external coordinate system B has many uses. In radiation therapy if the location of a tumor is known with respect to the internal coordinate system and the internal coordinate system is known with respect to an external coordinate system having a radiation source 20, such as an x-ray machine for killing cancer cells, then radiation can be applied only to the tumor provided it can concentrate on the volume of the tumor only. This would remove the guess work of a radiotherapist looking at various images of a tumor in a body and estimating where to aim the radiation source so, hopefully, only the tumor is irradiated. The location of a tumor in an internal coordinate system can be identified for instance, by a first imaging session. The data therefrom is stored in a medium that allows its recall when the tumor position is desired to be known and it is not desired to have to retake images of the anatomy.

Figure 8:
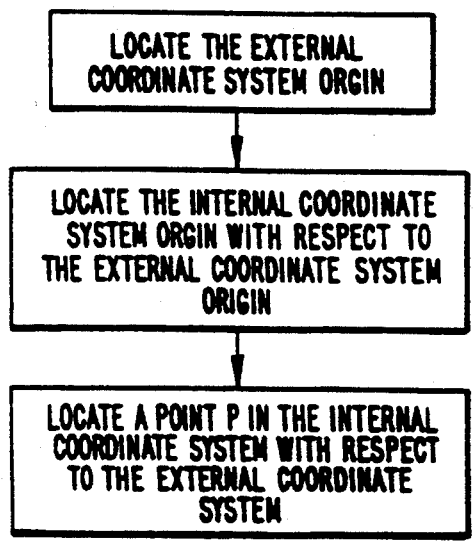
FIG. 8 is a flow chart with respect to determining the location of a point P in an internal coordinate system with respect to an external coordinate system.

One way to accomplish the irradiation of a specific location the body 32, where, for instance, a tumor is located, involves the use of a robot arm 34 whose base 36 can be chosen as the origin (0,0,0) of the external coordinate system B. At the tip 38 of the robot arm 34 is located a sensor 40. The sensor 40 can be a metal detector or an ultrasonic detector or any instrument that can sense the position of a fiducial implant 10 in a body 32. If the fiducial implants 10 are placed in a skull 18 and there is a tumor therein, the sensor 40 in the tip 38 of the robot arm 34 is moved by the arm 34 until it contacts a fiducial implant 10 in the skull 18. The movement of the robot arm 34 is tracked by a computer (not shown) so the position of the sensor 40 relative to the arm's 34 base 36, the origin 0 of the external coordinate B, is known. The means to track the arm is well known and is accomplished by sensors (not shown) in critical locations of the arm 34, detecting rotation or movement of the joints 42 of the arm 74. By supplying this information to a computer along with the information of the fixed lengths of the structure of the robot arm 34, the tip 38 location of the arm 34 is always known. When the tip 38 of the arm 34 rests on the fiducial implant 10 in the skull 18, the location of the internal coordinate system A defined by the fiducial implants 10 is known with respect to the external coordinate system B. Supplying the Euler angles of rotation and the location of the tumor which is known relative to the internal coordinate system A to the computer, provides the ability to determine the location of the tumor in the external coordinate system B (see FIG. 8). The location of the tumor is known relative to the internal coordinate system through for instance the image data already stored, and the fact that the fiducial implants 10 are also fixed relative to each other once they are in place. The radiation source 30 and where it is aimed is known by the computer relative to the external coordinate system B. The computer, having the information where the tumor is located in the external coordinate system B, can aim the radiation source 30 to precisely irradiate the tumor site in the brain. In general, the location of a point P in the internal coordinate system relative to the external coordinate system is determined when the distance between the origins of the two coordinate systems is known and the Euler angles are known, as described above.

In surgery, the internal coordinate system defined by the three fiducial points can allow, for example, a laser to be followed as it cuts through tissue to a tumor. An imaging system present in the operating theater would be positioned to continually take imaging data that is provided to a computer system which also guides the laser based on the inputted data. As the laser cuts through the tissue, the change in the tissue is apparent through the imaging system and can be followed with respect to the fixed internal coordinate system. When a predetermined position is reached by the laser, or a predetermined portion of tissue has been removed by the laser, the computer controlling the laser and processing the imaging data would discontinue the operation of the laser.

In the operation of the invention, after the fiducial implants are in place in a patient, imaging data is taken at a first time and stored. At distinct intervals in time, for instance about every year thereafter, the patient returns to the location of the imaging system, or one similar to it, and undergoes follow-up imaging. The most recently received imaging data is then reformatted, as described above, to obtain high fidelity images of the same cross-sections on the body as attained in the earlier session. The purpose of the comparisons, as stated earlier can be multifold: (a) either a simple follow-up of the growth of the tumor, without therapy; or (b) verification of therapeutic treatment, such as radiation or chemotherapy or (c) follow-up of surgical treatment.

In the operation of the invention with regard to radiation therapy, the tumor is first identified in the patient's body. The patient is then positioned in the imaging system such that at least the tumor area can be imaged. The imaging system is used to locate the position of the tumor in the internal coordinate system. The image data can, for instance, then be stored for later use so the tumor position is identified without new images having to be obtained every time radiation therapy is performed. The patient can then be placed before a radiation source, and each time radiation therapy occurs, the information from the imaging session that is stored is supplied to the computer operating the radiation source. The internal coordinate is located with respect to the external coordinate system, for instance by locating one fiducial implant, as described above, with respect to a known position in the external coordinate system. Once the position of the internal coordinate system is known with respect to the external coordinate system, the tumor position is known with respect to the external coordinate system from the stored imaging information. A radiation source is then aimed, for example by a computer receiving the imaging and position data, at the tumor in the body. With respect to surgery, the procedure that is followed to take advantage of the fiducial implants is similar to the procedure described above for directing radiation. Once the tumor is located with respect to the internal coordinate system, and the location of the internal coordinate system is known with respect to the external coordinate system, the tumor is located with respect to the external coordinate system. Surgical instruments can then be guided to the tumor by the computer with the imaging system placed in an interactive mode therewith. The imaging data that the imaging system constantly feeds the computer allows the computer to track the progress and the extent of the surgery.

In an alternative embodiment, while three fiducial implants 10 are the minimum necessary to define an internal coordinate system, there can be n fiducial implants 10, where n is greater than or equal to four and is an integer, that may be used. The advantage of using n fiducial implants 10 is that additional internal coordinate systems can be defined that result in increased clarity of images obtained from an imager by the proper choice of the coordinate system to maximize the same. This is essentially true with respect to the comparison of, for instance, an image from a magnetic resonance imager and an image of a CT imager concerning the same portion of a patient's anatomy. Depending on the distortion, if any, that is present in images that are obtained, three fiducial implants 10 can be picked from the n fiducial implants 10 that are present in a patient to provide the greatest clarity and image with respect to the patient. The internal coordinate system can be determined by choosing which three fiducial implants 10 of the n fiducial implants 10 provide an internal coordinate system which yields the clearest images or the best view of the portion of anatomy of interest. Additionally, once the three fiducial implants 10 are chosen of the n fiducial implants 10, it does not necessarily means that each image must be produced with respect to the coordinate system defined by these three fiducial implants 10. Instead, as each image is produced with respect to a certain portion of the anatomy of a patient, the various coordinate systems that are present due to there being n fiducial implants 10 can be reviewed, and for each image, the choice of the coordinate system that provides the most clarity can be chosen. Once the 3 fiducial implants 10 are chosen, then the internal coordinate system defined by them can be used as is described herein.

Obviously, numerous (additional) modifications and variations of the present invention are possible in light of the above teachings. It is therefore to be understood that within the scope of the appended claims, the invention may be practiced otherwise than as specifically described therein.

What is claimed is:

1. A method for transforming and displaying images of the anatomy comprising:
   providing a first set of actual reference markers by implanting at least three fiducial implants in spatial relationship to form a plane on a portion of the anatomy to be imaged;
   taking a first set of images of a set of parallel cross-sectional slices of fixed thickness of said portion of the anatomy, said set of slices including points in space corresponding to those occupied by said first set of actual reference markers, said first set of images forming a first set of data;
   storing said first set of data corresponding to said images in a storing device;
   taking a second set of images of parallel cross-sectional slices of fixed thickness of said portion of the anatomy including points in space corresponding to said first set of actual reference markers, said second set of images forming a second set of data;
   storing said second set of data corresponding to said second set of images in a storing device;
   transmitting data corresponding to said first set of data and said second set of data to a database library;
   displaying at least a first slice of said first set of images;
   providing a first set of additional reference markers by assigning a number of computer generated reference points to the first slice;
   localizing some of said first set of additional reference markers and said first set of actual reference markers in said first slice;
   displaying a second slice of said second set of data;
   providing a second set of additional reference markers by assigning a number of computer generated reference points to the second slice;
   localizing some of said second set of additional markers and said first set of actual reference markers in said second slice;
   labeling three of said first set of additional reference markers and said first set of actual reference markers in said first set of images at least one of which is from said first set of additional reference markers;
   labeling three of said second set of additional reference markers and said first set of actual reference markers in said second set of images at least one of which is from said second set of additional reference markers;
   calculating spatial transformation data relating said first set of images to said second set of images;
   storing said spatial transformation data in said database library;
   executing said spatial transformation of said second set of images with respect to said first set of images so that the second set of images is an spatial correspondence with said first set of images;
   displaying at least one of said transformed second set of images.

2. The method of claim 1, wherein up to nine computer generated reference points are provided to each slice of said first and second set of images.

3. The method of claim 1, wherein up to nine computer generated reference points are provided with the second slice.

4. The method of claim 1, further comprising:
   selecting a first point from either of said data sets;
   selecting a second point in the same data set; and
   computing the distance between the first and second data points.

5. The method of claim 1, wherein said calculating step includes the step of tracing a continuous line about a portion of a slice so that it may be displayed along with the slice.

6. An apparatus for imaging a portion of the anatomy comprising:
   three fiducial implants for use as spatial reference markers, said fiducial implants being adapted for implantation in spatial relationship to form a plane in a portion of the anatomy to be imaged;

means for taking a first series of images at parallel cross-sectional slices of fixed thickness of said portion of the anatomy with some of said slices being taken through said fiducial implants;

means for providing a first set of additional reference markers by assigning at least one computer generated reference point to at least one slice within the first said series of images, said means for providing additional reference markers defining a plane from three of said fiducial implants and said first set of additional reference markers, at least one of which is from said first set of additional reference markers;

means for storing a first set of data corresponding to said images in a storage device with reference to the plane established by said fiducial implants; and means for displaying at least one of said first series of images corresponding to said data for view by a user from said storage device.

7. The apparatus according to claim 6 further comprising:

means for taking a second series of images at parallel cross-section slices of fixed thickness of said portion of the anatomy with some of said slices being taken through said fiducial implants;

means for providing a second set of additional reference markers by assigning a number of computer generated reference points to at least one slice within the second series of images;

means for storing a second set of data corresponding to said second series of images in said storage device with reference to the plane established by said fiducial implants;

and wherein said means for displaying is capable of displaying at least one portion of said second set of images corresponding to said data from said storage device and said means for displaying includes means for displaying images corresponding to planes defined by three of said fiducial implants and said first and second set of additional reference markers.

8. The apparatus according to claim 7 wherein said means for displaying includes means for displaying at least one of said first series of images simultaneously with at least one of said second series of images.

9. The apparatus according to claim 8 further comprising means for calculating a transformation angle between said first series of images at parallel cross-sectional slices and said second series of images at parallel cross-sectional slices.

10. The apparatus according to claim 9 wherein said means for calculating the transformation angle includes means for selecting a first image from said first series of images, means for selecting a second image to be transformed from said second series of images, means for labeling three of said first set of additional reference markers and said fiducial implants in the selected second image, means for calculating the transformation of said second image to said first image, means for storing transformation data in data base library, and means for executing the transformation of said second image to said first image.

11. The apparatus according to claim 10 wherein said means for calculating the transformation includes transforming the entire second series of images and means for replacing the data corresponding to said second series of images with data corresponding to said transformation in said data base library.

12. The apparatus according to claim 11 further comprising means for displaying the transformation data on said means for displaying for comparison with data from said first image.

13. The apparatus according to claim 8 further comprising means for inputting test parameters and means for calculating a transformation angle of one displayed image according to said test parameters.

14. The apparatus according to claim 13 wherein said means for inputting test parameters includes means for inputting three eulerian angles associated with the transformation angle.

15. An apparatus for imaging the anatomy comprising:

three fiducial implants for use as reference markers, said fiducial implants being adapted for implantation in spatial relationship to form a plane on a portion of the anatomy to be imaged;

means for taking a first series of images of a set of parallel cross-sectional slices of fixed thickness of said portion of the anatomy that includes said reference markers, said first series of images constituting a first set of data;

means for providing at least one slice from said first series of images at least one computer generated reference point;

means for storing said first set of data corresponding to said images in a storing device;

means for taking a second set of images at parallel cross-sectional slices of fixed thickness of said portion of the anatomy, said second series of images including points in space corresponding to said fiducial markers and constituting a second set of data;

means for providing to at least one slice from said second set of images at least one computer generated reference point;

means for storing said second set of data corresponding to said second series of images in said storing device;

means for transmitting data corresponding to said first set of data and said second set of data to a database library;

means for displaying at least a first slice of said first set of images;

means for localizing some of said fiducial markers and computer generated reference points in said first slice;

means for displaying a second slice of said second set of data;

means for localizing three some of said fiducial markers and computer generated reference points in said second slice;

means for labeling three fiducial markers and computer generated reference points in said first slice;

means for labeling said three localized fiducial markers and computer generated reference points in said second slice;

means for calculating the spatial transformation data relating said first slice to said second slice based on said labeled fiducial markers and computer generated reference points;

means for storing said transformation data in a database library;

means for executing a spatial transformation of said second image with respect to said first image using said transformation data; and means for displaying said second transformed image.

16. The apparatus of claim 15, further comprising:
means for selecting a first point from either of said data sets;
means for selecting a second point in the same data set; and
means for computing the distance between the first and second data points.

17. The apparatus of claim 16, further comprising means for tracing a continuous line about a portion of a slice so that it may be displayed along with the slice, said means for tracing coupled to said means for displaying.

18. A method for transforming and displaying images of the anatomy comprising:
implanting at least three fiducial implants in spatial relationship to form a plane in a portion of an anatomy to be imaged;
taking a first set of images of a set of parallel cross-sectional slices of fixed thicknesses of said portion of the anatomy, said set of slices including points in space corresponding to points in space occupied by said fiducial implants, said first set of images forming a first set of data;
storing said first set of data corresponding to said first set of images in a storage device;
selecting at a user input device at least one of said first set of parallel cross-sectional slices for display on an image screen;
retrieving data from said storage device of said slices selected at said user input device;
displaying said slices selected at said user input device on said image screen;
selecting at said user input device three of said fiducial implants appearing in said slices displayed on said image screen;
localizing said fiducial implants selected at said user input device in said slices displayed on said image screen;
inputting transform parameters at said user input device; and
executing a spatial transformation of said first set of data in accordance with said transform parameters sufficiently to form a first set of modified data, said first set of modified data comprising cross-sectional slices of image data.

19. The method of claim 18 further comprising:
storing patient identification with said first set of data in said storage device; and
selecting a set of parallel cross-sectional slices of image data based on a desired patient identification.

20. The method of claim 18 further comprising:
displaying some of said cross-sectional slices of image data from said first set of modified data on said display screen.

21. A method for transforming and displaying images of the anatomy comprising:
implanting at least three fiducial implants in spatial relationship to form a plane in a portion of an anatomy to be imaged;
taking a first set of images of a set of parallel cross-sectional slices of fixed thickness of said portion of the anatomy, said first set of slices including points in space corresponding to points in space occupied by said fiducial implants, said first set of images forming a first set of data;
storing said first set of data corresponding to said first set of images in a storage device;
selecting at a user input device at least one of said first set of parallel cross-sectional slices for display on an image screen;
retrieving data from said storage device of said slices from said first set of images selected at said user input device;
displaying said slices from said first set of images selected at said user input device on said image screen;
selecting at said user input device three of said fiducial implants appearing in said slices from said first set of images displayed on said image screen;
localizing said fiducial implants selected at said user input device in said slices from said first set of imaged displayed on said image screen;
taking a second set of images of a set of parallel cross-sectional slices of fixed thickness of said portion of the anatomy, said second set of slices including points in space corresponding to points in space occupied by said fiducial implants, said second set of images forming a second set of data;
storing said second set of data corresponding to said second set of images in said storage device;
selecting at said user input device at least one of said second set of parallel cross-sectional slices for display on said image screen;
retrieving data from said storage device of said slices from said second set of images selected at said user input device;
displaying said slices from said second set of images selected at said user input device on said image screen;
selecting at said user input device three of said fiducial implants appearing in said slices from said second set of data displayed on said image screen;
localizing said fiducial implants selected at said user input device in said slices from said second set of data displayed on said image screen;
calculating spatial transformation data relating said slices from said first set of data to said slices from said second set of data;
storing said spatial transformation data in said storage device; and
executing transformation of said first set of data to said second set of data using said spatial transformation data, such that said second set of data is in spatial correspondence with said first set of data.

22. The method of claim 21, further comprising:
storing patient identification information with said first and second sets of data in said storage device; and
selecting sets of parallel cross-sectional slices of image data based on desired patient identification information.

23. The method of claim 22 further comprising:
displaying some of said cross-sectional slices of image data from said first and second sets of data on said display screen after executing transformation of said first set of data to said second set of data using said spatial transformation data.

* * * * *